(12) United States Patent
Canova et al.

(10) Patent No.: US 9,492,373 B2
(45) Date of Patent: Nov. 15, 2016

(54) COSMETIC COMPOSITION CONTAINING A DISPERSION OF POLYMER PARTICLES AND MINERAL FILLERS

(71) Applicant: RHODIA POLIAMIDA E ESPECIALIDADES LTDA, Sao Paolo (BR)

(72) Inventors: Thomas Gonzaga Canova, Sao Paolo (BR); Gabriel Gorescu, Sao Paolo (BR); Tarcis Cordeiro Bastos, Sao Paolo (BR)

(73) Assignee: RHODIA POLIAMIDA E ESPECIALIDADES LTDA, Sao Paulo (BR)

( * ) Notice: Subject to any disclaimer, the term of this patent is extended or adjusted under 35 U.S.C. 154(b) by 8 days.

(21) Appl. No.: 14/401,925

(22) PCT Filed: May 21, 2013

(86) PCT No.: PCT/IB2013/000989
§ 371 (c)(1),
(2) Date: Nov. 18, 2014

(87) PCT Pub. No.: WO2013/175286
PCT Pub. Date: Nov. 28, 2013

(65) Prior Publication Data
US 2015/0147364 A1   May 28, 2015

(30) Foreign Application Priority Data
May 22, 2012   (FR) .................. 12 54657

(51) Int. Cl.
| A61K 8/96 | (2006.01) |
| A61K 8/26 | (2006.01) |
| A61K 8/29 | (2006.01) |
| A61Q 19/08 | (2006.01) |
| A61K 8/88 | (2006.01) |
| A61K 8/02 | (2006.01) |
| A61K 8/19 | (2006.01) |
| A61K 8/04 | (2006.01) |
| A61Q 19/00 | (2006.01) |

(52) U.S. Cl.
CPC ............. *A61K 8/965* (2013.01); *A61K 8/0283* (2013.01); *A61K 8/04* (2013.01); *A61K 8/19* (2013.01); *A61K 8/26* (2013.01); *A61K 8/29* (2013.01); *A61K 8/88* (2013.01); *A61Q 19/00* (2013.01); *A61Q 19/08* (2013.01); *A61K 2800/412* (2013.01); *A61K 2800/654* (2013.01)

(58) Field of Classification Search
None
See application file for complete search history.

(56) References Cited

U.S. PATENT DOCUMENTS

| 4,999,243 A | 3/1991 | Maeda |
| 5,658,579 A * | 8/1997 | LaFleur .................. A61K 8/25 424/401 |
| 6,316,102 B1 * | 11/2001 | Sasaki ...................... D01F 2/06 428/364 |
| 2007/0141095 A1 * | 6/2007 | Simonnet ............... A61K 8/027 424/401 |

FOREIGN PATENT DOCUMENTS

| EP | 2402387 A1 | 1/2012 |
| KR | 20060081174 A | 7/2006 |
| KR | 20070006549 A | 1/2007 |

OTHER PUBLICATIONS

English Translation of International Search Report corresponding to International Patent Application No. PCT/IB2013/000989, mailed Aug. 5, 2014, 3 pages.

* cited by examiner

*Primary Examiner* — Robert A Wax
*Assistant Examiner* — Quanglong Truong
(74) *Attorney, Agent, or Firm* — Dentons US LLP

(57) ABSTRACT

A cosmetic composition is described that includes particles of a polymeric composition that includes a polymer matrix and one or a plurality of mineral filler(s), uniformly dispersed in the polymer matrix, having properties of absorption and/or emission in the far infrared region ranging from 2 μm to 20 μm. The particles of the polymeric composition can be dispersed in a carrier fluid including water and/or one or a plurality of organic fluids. The composition is, for example, intended to prevent or reduce the signs of skin aging.

48 Claims, No Drawings

COSMETIC COMPOSITION CONTAINING A DISPERSION OF POLYMER PARTICLES AND MINERAL FILLERS

CROSS-REFERENCE TO PRIOR APPLICATIONS

This application is a National Stage of PCT/IB2013/000989, filed May 21, 2013, and designating the United States (published on Nov. 28, 2013, as WO 2013/175286 A2), which claims priority under 35 U.S.C. §119 to French Patent Application 1254657, filed May 22, 2012, each hereby expressly incorporated by reference in its entirety and each assigned to the assignee hereof.

The subject of the present invention is a cosmetic composition, which comprises a dispersion of particles of a polymeric composition in which are dispersed one or more mineral filler(s) which have properties of absorption and/or emission of radiation in the far infrared range.

The subject of the present invention is also the use of such a composition for preventing or reducing the signs of skin aging, and in particular for combating wrinkles.

It is known that the appearance of human skin changes over time, owing to natural aging phenomena, which can be accelerated by external factors such as pollution and lifestyle (for example diet, stress, smoking).

This aging of the skin results in particular in the appearance, at its surface, of various marks such as more or less deep wrinkles, and spots known as "age spots".

These marks of skin aging are increasingly considered to be unattractive, in particular those located on the parts of the body that show, such as the face, the neck and the hands.

Thus, numerous cosmetic products have been developed for preventing the appearance of the signs of skin aging and/or reducing those already present. These products are generally in the form of compositions which are more or less thick fluids, such as creams, lotions or sera, which contain one or more antiwrinkle active agents dispersed or dissolved in an aqueous-based and/or organic-based fluid. These active agents are chemical or natural compounds intended for combating wrinkles and/or spots. These cosmetic products must generally be applied to the areas to be treated once or twice a day, and have very variable degrees of effectiveness.

Despite the numerous products currently present on the market, the consumer is still searching for innovative and effective solutions which can be used in place of or as a supplement to the already existing solutions. There is thus a need to provide new solutions, which make it possible to effectively combat skin aging.

Pursuing its research in this field, the Applicant has now discovered a novel and original approach, which makes it possible to effectively combat the signs of skin aging, in particular wrinkles and age spots.

This approach is based on the use of a particular polymeric composition, comprising a polymer matrix within which are dispersed mineral fillers which emit and/or absorb infrared radiation in the wavelength range located between 2 µm and 20 µm.

This polymeric composition is dispersed under the form of particles in the base fluid of a cosmetic composition intended to be applied to the skin.

Indeed, the Applicant has discovered, totally unexpectedly, that the application to the skin of such a dispersion of particles formed from said polymeric composition has the effect of reducing the signs of aging already present on the skin, and of preventing or delaying the appearance of new signs.

The subject of the present invention is therefore a cosmetic composition, comprising particles of a polymeric composition which contains a polymer matrix and one or more mineral filler(s), uniformly dispersed in the polymer matrix, having properties of absorption and/or emission in the far infrared region ranging from 2 µm to 20 µm, said particles of polymeric composition being dispersed in a carrier fluid comprising water and/or one or more organic fluids.

The subject of the present invention is also a cosmetic treatment method for the skin, consisting in bringing the skin into contact with a cosmetic composition as described in the present application.

The subject of the present invention is finally the use of such a cosmetic composition for preventing and/or reducing the signs of skin aging.

In a manner known per se, the term "signs of skin aging" denotes the marks present on the skin resulting from aging phenomena, which modify its visual appearance and are generally considered to be unattractive, such as, in particular, wrinkles and age spots.

The cosmetic composition according to the invention exhibits excellent effectiveness for combating such signs of skin aging.

It also has the advantage of being particularly soft when it is applied to the skin, and non-irritant to said skin. In particular, the incorporation of mineral fillers into a polymeric composition makes the composition softer, and less abrasive to the skin, than if these same fillers were directly dispersed in the carrier fluid.

Finally, the dispersion of the mineral fillers in the carrier fluid is more homogeneous, and more stable over time, when these fillers are incorporated into particles of polymeric composition in accordance with the present invention.

The invention uses a polymeric composition comprising a polymer matrix.

The polymer matrix can be chosen in particular from the group comprising: polyesters, polyolefins, polymers based on a cellulose ester, such as cellulose acetate, cellulose propionate, rayon, viscose and polymers of the same family, acrylic polymers and copolymers, polyamides such as polyhexamethylene adipamide (PA66), polycaproamide (PA6), PA6.10, PA10.10 and PA12, copolymers in any proportions of these polymers, and blends between any of these polymers.

According to one preferential embodiment, the polymer matrix consists of polyamide, preferably chosen from polyamide 6, polyamide 66 and copolymers of polyamide 6/polyamide 66 in any proportions.

The polymeric composition according to the invention comprises one or more mineral filler(s) having properties of absorption and/or emission in the far infrared region ranging from 2 to 20 µm. Preferably, the mineral filler(s) has (have) properties of absorption and/or emission in the far infrared region ranging from 3 to 20 µm, and even more preferentially from 3 to 15 µm.

According to the invention, the mineral filler(s) is (are) uniformly dispersed in the polymer matrix. The term "uniformly dispersed" is intended to mean that the mineral fillers are homogeneously incorporated actually into the polymer. In particular, the particles are trapped in the polymer composition. They are not therefore mineral fillers deposited on the polymer, for example in the form of a coating at the surface of the polymer.

Such a uniform dispersion can be obtained by incorporating the mineral filler(s) into the polymer during the synthesis of the latter. One embodiment consists in producing one or more surfactant-stabilized suspension(s) of mineral fillers. The suspension(s) is (are) then added during the synthesis of the polymer.

Said fillers can also be incorporated by mixing the latter with the molten polymer, either directly, or by means of a concentrate of particles in the form of a masterbatch, it being possible for the latter to be subsequently diluted to predetermined concentrations in the polymer mass.

By virtue of such processes, it is possible to obtain polymeric compositions according to the invention which contain the mineral filler(s) in a manner uniformly dispersed in the polymer matrix.

The mineral filler(s) usable according to the invention can be chosen in particular from oxides, sulfates, carbonates, phosphates and silicates.

Preferably, the oxide(s) is (are) chosen from titanium dioxide, silicon dioxide and magnesium oxide.

The sulfate(s) can advantageously be chosen from alkali metal and alkaline-earth metal sulfates, preferably from barium sulfate, calcium sulfate and strontium sulfate.

The carbonate(s) is (are) advantageously chosen from calcium carbonate and sodium carbonate.

Preferably, the silicate(s) is (are) chosen from actinolite, tourmaline, serpentine, kaolinite, and zirconium silicate.

The phosphate(s) can be chosen from zirconium phosphates, cerium phosphate and apatite, and mixtures thereof.

Preferably, the polymeric composition contains at least two mineral fillers of different types, chosen from the following types: oxides, sulfates, carbonates, phosphates and silicates. Particularly preferably, the polymeric composition contains at least three mineral fillers of different types, chosen from the abovementioned types.

According to a first preferred embodiment, the polymeric composition contains at least two mineral fillers of different types, chosen from the following types: oxides, sulfates and silicates, and preferably from titanium dioxide, an alkali metal or alkaline-earth metal sulfate and a silicate, and even more preferably from titanium dioxide, barium sulfate and tourmaline.

More preferably, the polymeric composition contains at least three mineral fillers of different types, chosen from the above types. Particularly preferably, the polymeric composition contains three mineral fillers of different types, which are an oxide, a sulfate and a silicate.

Preference is given quite particularly to the titanium dioxide/alkaline-earth metal sulfate/silicate combination, and even more preferentially the titanium dioxide/barium sulfate/tourmaline combination.

In this case, the respective weight proportions of the three mineral fillers above are preferably between 80:10:10 and 10:30:60, and more specifically these respective proportions are 50:25:25.

According to a second embodiment, which is also advantageous, the polymeric composition contains at least two mineral fillers of different types, and preferably at least three mineral fillers of different types, chosen from the following types: oxides, phosphates and silicates.

In this embodiment, combinations of three mineral fillers of different types, namely an oxide, a phosphate and a silicate, are particularly preferred.

Preferably, the weight proportion of mineral filler(s) relative to the total weight of the polymeric composition is greater than or equal to 1.0%, preferably greater than or equal to 1.5% and even more preferentially greater than or equal to 2.5%.

Preferably, the weight proportion of mineral filler(s) relative to the total weight of the polymeric composition is less than or equal to 50%, preferably less than or equal to 40% and even more preferentially less than or equal to 30%.

The mineral filler(s) according to the invention is (are) advantageously in the form of particles, which preferably have a volume-average size of less than or equal to 2 µm, measured according to the laser diffraction particle size analysis method (using, for example, Malvern or Cilas particle size analyzers).

One advantageous way to carry out the process consists in suspending the particles in water and in determining their particle size by laser diffraction using the method described in standard ISO 13320:2009.

It is preferable for the mineral fillers used in the present invention to have a particle size which is:
  neither too small, so as to prevent any risk of the particles being able to leave the polymer matrix and introduce themselves into the human body through the skin or via the airways, or else disperse in the environment;
  nor too large, which would make the incorporation of the particles into the polymer matrix more difficult and especially might make the cosmetic composition abrasive on contact with the skin, which might in the end have an irritant effect on the skin, for example in the case of particularly thin or sensitive skin.

Thus, the mineral filler(s) according to the invention are in the form of particles which advantageously have a volume-average size, measured according to the laser diffraction particle size analysis method, ranging from 0.1 to 2 µm, more preferentially from 0.2 to 1.5 µm and even more preferentially from 0.2 to 1 µm.

The mineral fillers advantageously have a particle size distribution with 99% by volume of the particles having a size of less than 1.0 µm, preferably 90% by volume of the particles having a size of less than 0.5 µm. The particle size distribution is also measured by the abovementioned laser diffraction particle size analysis method (using, for example, Malvern or Cilas particle size analyzers).

The polymeric composition according to the invention preferably has more than 10 infrared radiation absorption peaks in the following ten frequency ranges: 3.00+/−0.30 µm, 6.20+/−0.50 µm, 8.00+/−0.25 µm, 8.50+/−0.25 µm, 9.00+/−0.25 µm, 9.50+/−0.25 µm, 10.00+/−0.25 µm, 10.50+/−0.25 µm, 11.00+/−0.25 µm, 14.60+/−2.10 µm, at least 1 peak being present in at least 7 of these ten frequency ranges.

The infrared radiation absorption spectrum can be determined by any method known to those skilled in the art. One possible method is the use of a Bruker Equinox 55 instrument, with a resolution of 4 $cm^{-1}$. In this case, the spectrum obtained is in ATR ("Attenuated Total Reflectance") form, using a ZnSe crystal.

As has been set out above, the composition according to the invention contains particles of a polymeric composition.

These particles of polymeric composition are present in a content which can range from 0.5% to 20% by weight, preferably from 1% to 15% by weight and more preferentially from 2% to 10% by weight, relative to the total weight of the cosmetic composition.

These particles of polymeric composition can have any shape and any size compatible with an incorporation and a dispersion in a carrier fluid in a cosmetic composition intended to be applied to the skin.

According to a first preferred embodiment of the invention, the particles of polymeric composition have a substantially spherical shape, i.e. the particles have a shape similar to that of a sphere, which may be more or less regular, for example ovalized and/or flattened.

In this embodiment, the particles of polymeric composition advantageously have a volume-average size of less than or equal to 250 µm, preferably ranging from 5 to 150 µm and preferentially from 10 to 50 µm.

The volume-average size of the particles of polymeric composition is measured according to the abovementioned laser diffraction particle size analysis method (using, for example, Malvern or Cilas particle size analyzers).

In this embodiment, the ratio between the volume-average size of the particles of polymeric composition and the volume-average size of the mineral fillers can also be optimized so as to avoid any risk of the particles being too small and being able to leave the polymer matrix and introduce themselves into the human body or disperse in the environment, or, on the contrary, being too large, with the risk of making the composition abrasive on contact with the skin.

Thus, the ratio between the volume-average size of the particles of polymeric composition according to the invention and the volume-average size of the mineral fillers, these two sizes being measured according to the abovementioned laser diffraction particle size analysis method, is advantageously greater than or equal to 5. This ratio is preferably less than or equal to 250. This ratio preferably ranges from 5 to 150, more preferentially from 5 to 100.

The particles of polymeric composition according to the invention can be prepared by the methods known to those skilled in the art for obtaining powders or fine particles of polymers, for example by milling, cryomilling or spray drying of the polymeric composition. Alternatively, the method described in patent application FR 2 899 591 in the name of the Applicant, the content of which is incorporated into the present application by way of reference, can be used.

According to a second preferred embodiment of the invention, the particles of polymer composition have the shape of fibers, the average length of which is preferably less than or equal to 3 mm, more preferentially less than or equal to 2 mm and even more preferentially less than or equal to 1.5 mm.

These fibers preferably have an equivalent average diameter ranging from 4 to 50 µm, preferably from 6 to 30 µm and more preferentially from 6 to 20 µm.

These two parameters (the average length and the equivalent average diameter of the fibers) are advantageously measured by optical microscopy.

In this second embodiment, the ratio between the size of the mineral filler(s) and the diameter of the fibers can also be optimized so as to avoid any risk of the particles being too small and being able to leave the polymer matrix and introduce themselves into the human body or disperse in the environment, or, on the contrary, being too large, with the risk of making the composition abrasive on contact with the skin.

Thus, the ratio between the equivalent average diameter of the fibers according to the invention and the volume-average size of the mineral fillers, measured according to the abovementioned laser diffraction particle size analysis method, is then advantageously greater than or equal to 10. This ratio between the equivalent average diameter of the fibers and the volume-average size of the mineral fillers is preferably less than or equal to 200.

The fibers according to the invention can be prepared by methods known to those skilled in the art. The process can, for example, be carried out by melt spinning of the polymeric composition, so as to obtain filaments, which are then cut up (by means of a guillotine device or any other means known to those skilled in the art) so as to obtain fibers having the desired length.

It should be noted that, whatever the shape of the particles of polymeric composition according to the invention, the incorporation of the mineral fillers into the polymer matrix is advantageously carried out before the actual forming of the polymer, in order to guarantee that the mineral fillers are well dispersed in the polymer matrix.

As explained above, the particles of polymeric composition according to the invention are used in the form of a dispersion in a cosmetic composition.

This dispersion is produced by dispersing said particles in a carrier fluid, i.e. a liquid medium which serves as a vehicle for said particles. This carrier fluid comprises water and/or one or more organic fluids.

According to the invention, the term "organic fluid" denotes organic liquids which can have very variable viscosities. Thus, the organic fluids usable in the invention can have a dynamic viscosity at 20° C. ranging from $10^{-4}$ to $10^{3}$ Pa·s, preferably from $0.5 \times 10^{-3}$ to $10^{2}$ Pa·s.

Such fluids can be water-miscible in any proportions. They can thus be chosen from monoalcohols containing from 2 to 4 carbon atoms, and polyols containing from 2 to 6 carbon atoms, such as, in particular, glycol, glycerol or sorbitol.

Such fluids can also be water-immiscible, and in this case, when the composition also contains water, said composition is then in the form of an emulsion. They can thus be chosen from natural or synthetic oils, in particular mineral oils, vegetable oils, fatty alcohols, fatty acids, esters containing at least one fatty acid and/or at least one fatty alcohol, and silicones.

The alcohols and acids mentioned above are those which contain from 8 to 32, preferably from 10 to 26 and more preferentially from 12 to 22 carbon atoms.

It is of course possible to use mixtures of organic fluids and in particular any mixtures of any of the fluids described above.

According to one particularly preferred embodiment, the carrier fluid contains water.

In this case, the cosmetic composition according to the invention advantageously contains at least 20% by weight of water, more preferentially at least 30% by weight of water and even more preferentially at least 50% by weight of water, relative to the total weight of said composition.

Likewise preferably, the cosmetic composition according to the invention contains, in addition to the water, one or more organic fluids.

In this case, the cosmetic composition according to the invention advantageously contains at least 5% by weight of organic fluid(s), more preferentially at least 10% by weight of organic fluid(s), relative to the total weight of said composition.

The cosmetic composition can also comprise all the conventional ingredients known to those skilled in the art as being part of the composition of cosmetic skin products. These ingredients can in particular, and in a nonlimiting way, be chosen from: thickeners, surfactants, moisturizing agents, skin conditioning agents, UV-screening agents, colored or noncolored pigments, antioxidants and preservatives.

The additional ingredients which can be used in the compositions according to the invention can in particular be chosen from those described in the International Cosmetic Ingredient Dictionary and Handbook, regularly published by The Cosmetic, Toiletry, and Fragrance Association.

According to one particularly advantageous embodiment, the cosmetic composition according to the invention also comprises one or more antiwrinkle active agents different from the mineral fillers according to the invention.

Indeed, the Applicant has noted a synergistic effect between the particles of polymeric composition according to the invention and the antiwrinkle active agents.

Such antiwrinkle active agents can in particular be chosen, in a nonlimiting manner, from:
retinoids, such as retinol, esters of a $C_2$ to $C_{22}$ acid and of retinol (for example, retinyl palmitate, retinyl acetate, retinyl propionate), retinal, retinoic acids;
natural or synthetic peptides, preferably those containing from 2 to 20 amino acids and/or amino acid derivatives, more preferentially from 2 to 10 amino acids and/or amino acid derivatives; the amino acid derivatives which may be present in oligopeptides are well known to those skilled in the art and include, inter alia, the isomers, esters and complexes, in particular metal complexes, of such amino acids;
alpha-hydroxy acids and beta-hydroxy acids (for example glycolic acid);
ketone acids (for example pyruvic acid);
hyaluronic acid, salts thereof (in particular sodium or potassium salts) and esters thereof.

The antiwrinkle active agents can be present in contents ranging from 0.01% to 10% by weight, preferably from 0.1% to 8% by weight and more preferentially from 0.5% to 5% by weight, relative to the total weight of the cosmetic composition of the invention.

The cosmetic composition according to the invention can be in very different forms, such as in particular, and in a nonlimiting way, liquids which are more or less viscous (such as fluids, milks or sera), lotions, more or less thick creams, pastes, gels, foams or sprays (sprayable compositions).

It can be a product intended essentially for skincare and/or for making up the skin (for example, a foundation, lipstick, face powder or eyeshadow composition).

According to one particularly preferred embodiment, the composition according to the invention is in the form of a cream, which preferably consists of an emulsion, and more preferentially of an oil-in-water emulsion.

The cosmetic composition according to the invention can be prepared by the methods known to those skilled in the art in the field of cosmetic product preparation. These methods generally comprise mixing the ingredients of the composition in one or more steps, and can also include heating and/or cooling steps.

The subject of the present invention is also a cosmetic treatment method for the skin, consisting in bringing the skin into contact with a cosmetic composition as described above.

This method consists in particular in applying said cosmetic composition to the skin, on the area(s) to be treated. This application can be daily, twice daily (for example, morning and evening), or more episodic (every other day, once a week, etc).

After application to the skin, the composition can either be left on, or rinsed off after a leave-on time which can range from a few minutes to a few hours.

The subject of the present invention is finally the use of such a cosmetic composition for preventing or reducing the signs of skin aging.

The detailed description, given above, of the method according to the invention also applies to the use according to the invention.

The examples of implementation of the invention below are given purely by way of illustration, and could not in any way be limiting in nature.

EXAMPLES

Example 1

Production of Particles of Polymeric Composition

The materials used are as follows:
PA66 polymer of relative viscosity 2.6;
Tourmaline (volume-average particle size of 0.8 µm);
Barium sulfate (volume-average particle size of 0.8 µm);
Titanium dioxide (volume-average particle size of 0.3 µm);
Additive A: Polyamide/polyalkylene oxide hydrophilic star copolymer obtained in the following way:

The following are introduced into a 7.5-liter autoclave equipped with a mechanical stirrer: 1116.0 g of s-caprolactam (9.86 mol), 57.6 g of 1,3,5-benzenetricarboxylic acid (0.27 mol), 1826.4 g of Jeffamine M2070 (0.82 mol), 1.9 g of Ultranox 236 and 3.5 g of an aqueous 50% (w/w) solution of hypophosphorous acid.

The reaction mixture is brought to 250° C. under nitrogen and at atmospheric pressure and maintained at this temperature for 1 h. The system is then gradually placed under vacuum for 30 min until a pressure of 5 mbar is obtained, and then maintained under vacuum for a further one hour. The system is then poured onto a plate.

Polyethylene oxide having a molecular weight of 400 g/mol.

Preparation of the Polymer Composition

The polyamides is mixed with the tourmaline, the barium sulfate and the titanium dioxide in such a way that the final weight composition is 70% of PA66, 2.7% of tourmaline, 6.8% of barium sulfate and 20.5% of titanium dioxide. The mixture is remelted in a twin-screw extruder at a temperature of 290° C. and extruded so as to obtain the granulated polymer.

Preparation of Particles of Polymeric Composition 10 µm in Size

The following are introduced into a 24D twin-screw extruder of Prism type: granules of the polymer composition obtained above, using feeding by volume, and a mixture of pellets of the additive A (weight concentration of 5%) and of polyethylene oxide (weight concentration of 19%), using feeding by weight. The mixture is extruded at a fixed flow rate of 2.0 kg/hour. The temperatures of the various zones of the extruder are between 275 and 295° C. The speed is set at 200 rpm. The pressure recorded is between 10 and 13 bar. The rods obtained are quenched at the die outlet with a stream of water, collected in a metal basket, drained and then dried.

The rods collected are then dispersed in water by simple mechanical stirring. The resulting dispersion is sieved with a 200 µm sieve to remove the large solid impurities, such as nondispersible pieces of rod. The yields by weight for recovery of polyamide polymer after sieving are greater than 90%. The particle size distribution of the particles contained in the dispersion was measured using a MasterSizer 2000 device sold by the company Malvern Instruments. This distribution, expressed by volume, obtained after application of ultrasound, is unimodal and the value of the modal peak is 10 μm.

Particles of polymeric composition containing 70% by weight of PA66 and 30% by weight of mineral fillers (titanium dioxide, barium sulfate, tourmaline) are thus obtained.

Example 2

Cosmetic Compositions According to the Invention

The three compositions below were prepared, from the ingredients indicated, for each, in the corresponding table below. For each composition, the content of each ingredient is indicated as a weight percentage, relative to the total weight of the composition.

The particles of polymeric composition used are those prepared according to example 1.

Example 2.1

Anti-Aging Emulsion

| Ingredients | Content by weight |
|---|---|
| Phase A | |
| Deionized water | 74.1% (qs 100%) |
| Crosslinked acrylic acid polymer (sold under the name Carbopol Ultrez 10 by the company Noveon) | 0.1% |
| Cetearyl glucoside (sold under the name Tego Care CG90 by the company Evonik) | 1.0% |
| Glycerol | 3.0% |
| Phase B | |
| Ethylhexyl stearate (sold under the name Tegosoft by the company Evonik) | 6.5% |
| Liquid paraffin | 5.0% |
| Stearic acid | 1.0% |
| Phase C | |
| Palmitoyl oligopeptides/Ceramide 2/$C_{12}$-$C_{15}$ alkyl benzoate/Tribehenin/PEG-10 rapeseed sterol (product sold under the name Dermaxyl by the company Sederma) | 2.0% |
| Phase D | |
| Deionized water | 3.5% |
| Preservatives | 0.3% |
| Phase E | |
| Particles of polyamide 66 containing mineral fillers (example 1) | 3.5% |
| Phase F | |
| 10% NaOH | q.s. pH = 6 |

This composition was prepared in the following way: the acrylic acid polymer was dispersed in the water, then, after 20 min of stirring, the cetearyl glucoside and the glycerol were added. The mixture was then heated to 75° C.

Phase B was prepared separately, by mixing its ingredients at 75° C.

Phase C was then heated to 75° C., and added to phase B, and the mixture was homogenized at 75° C., and then added to phase A.

The resulting mixture was homogenized at 75° C., then cooled to 35° C.

The ingredients of phase D were premixed, then added to the above mixture.

Phase E (polyamide particles) was then gradually added to the mixture, with stirring.

The pH was adjusted by means of phase F.

Example 2.2

Moisturizing Face Milk

| Ingredients | Content by weight |
|---|---|
| Phase A | |
| Glycerol at 96% in water | 9.50% |
| Xanthan gum (product sold under the name Keltrol CG by the company CP Kelko) | 0.15% |
| Lithium magnesium sodium silicate (product sold under the name Lucentite SWN by the company Kobo Products) | 0.50% |
| Particles of polyamide 66 containing mineral fillers (example 1) | 2.80% |
| Disodium EDTA | 0.10% |
| Deionized water | qs 100% |
| Phase B | |
| Glyceryl stearate (product sold under the name Lipomulse 165 by the company Lipo Chemicals) | 5.00% |
| Ethylhexyl methoxycinnamate (product sold under the name Parsol MCX by the company Parsol) | 7.50% |
| Stearyl alcohol (product sold by the company Rita) | 2.00% |
| 50/50 Cetearyl alcohol (product sold by the company Rita) | 0.75% |
| Isocetyl stearate (product sold under the name Crodamol ICS by the company Croda) | 4.00% |
| Cyclopentasiloxane/Cyclohexasiloxane (product sold under the name SF1256 by the company Kobo Products) | 4.50% |
| Phase C | |
| Triethanolamine | 2.25% |
| Deionized water | 2.00% |
| Phase D | |
| Cyclopentasiloxane/Titanium dioxide/Alumina/PEG-10 dimethicone/Lauryl polyglyceryl-3 polydimethylsiloxyethyl dimethicone/Methicone (product sold under the name CM3KG40T7 by the company Kobo Products) | 5.50% |
| Phase E | |
| Preservatives (methyl and propyl parabens) | 1.25% |
| Phase F | |
| Sodium hyaluronate in solution at 1% in water | 0.50% |
| Mica/Titanium dioxide/Poly(methyl methacrylate) (product sold under the name SK-45-R by the company Kobo Products) | 1.00% |
| Fragrance | 0.50% |

This composition was prepared in the following way: the lithium magnesium sodium silicate and the disodium EDTA are added to the water with stirring. The glycerol and the xanthan gum are premixed, then added to the main mixture with stirring. The mixture is then heated to 75-78° C., the polyamide particles are then added and everything is mixed for 15 minutes.

The ingredients of phase B are premixed separately and heated to 78-82° C. with stirring. Phase B is then added to phase A, and everything is mixed with stirring for 15 minutes.

The ingredients of phase C are premixed separately, then added to the main mixture after cooling of the latter to 65° C.

After cooling of the main mixture to 60° C., phase D is then added, and then, after 15 minutes of mixing, phase E is added.

After cooling of the main mixture below 50° C., the ingredients of phase F are added, then the mixture is homogenized for 10 minutes, and the resulting composition is left to cool to ambient temperature with stirring.

Example 2.3

Antiwrinkle Composition

| Ingredients | Content by weight |
|---|---|
| Phase A | |
| Cyclopentasiloxane/PEG/PPG-20/15 Dimethicone (product sold under the name SF1528 by the company Kobo Products) | 11.00% |
| Cyclopentasiloxane (product sold under the name SF1202 by the company Kobo Products) | 9.00% |
| Cyclopentasiloxane/Dimethicone (product sold under the name SF1214 by the company Kobo) | 7.50% |
| Phase B | |
| Particles of polyamide 66 containing mineral fillers (example 1) | 7.50% |
| Phase C | |
| Glycerol (Glycerin U.S.P. Natural 96%, sold by the company Univar USA Inc.) | 8.00% |
| Sodium chloride | 1.00% |
| Butylene glycol/Water/Palmitoyl hydroxypropyltrimonium amylopectin/Glycerol polymer/Polysorbate20/Retinol/ Phenoxyethanol/Parabens/Hydrogenated lecithin/BHT/BHA (product sold under the name Gs-VA100C by the company Kobo Products) | 0.50% |
| Water/Papain/Palmitoyl hydroxypropyltrimonium amylopectin/Crosslinked glycerol polymer/ Phenoxyethanol/Hydrogenated lecithin/Parabens (product sold under the name GsPPY by the company Kobo Products) | 0.50% |
| Polysorbate 80 (product sold under the name Liposorb O-20 by the company LIPO Chemicals) | 0.20% |
| Quaternium-15 (product sold under the name Dowicil 200 by the company DOW Chemical) | 0.10% |
| Deionized water | qs 100% |

This composition was prepared in the following way: the compounds of phase A were mixed, and the mixture was homogenized for 15 minutes. The polymer particles (phase B) were then added, and the homogenization was continued for 15 minutes.

The ingredients of phase C were premixed separately, then gradually added to the main mixture in five portions, while observing a mixing time of 15-20 minutes between each addition.

After complete homogenization of the mixture, the resulting composition was then packaged, by pouring it into appropriate containers.

The invention claimed is:

1. A cosmetic composition, comprising particles of a polymeric composition which comprises a polymer matrix and at least two mineral fillers of different types selected from the group consisting of oxides, sulfates, carbonates, phosphates and silicates, said mineral fillers being uniformly dispersed in the polymer matrix and having properties of absorption and/or emission in the far infrared region ranging from 2 μm to 20 μm, and said particles of the polymeric composition being dispersed in a carrier fluid comprising water and/or one or more organic fluids.

2. The composition as claimed in claim 1, wherein the polymer matrix is selected from the group consisting of polyesters, polyolefins, polymers based on cellulose esters, acrylic polymers and copolymers, polyamides, copolymers thereof and blends thereof.

3. The composition as claimed in claim 1, wherein the polymer matrix comprises a polyamide.

4. The composition as claimed in claim 1, wherein the at least two mineral fillers of different types are selected from the group consisting of: oxides, sulfates and silicates.

5. The composition as claimed in claim 1, wherein the polymeric composition comprises three mineral fillers of different types, which are an oxide, a sulfate and a silicate.

6. The composition as claimed in claim 1, wherein the polymeric composition comprises at least two mineral fillers of different types selected from the group consisting of: oxides, phosphates and silicates.

7. The composition as claimed in claim 1, wherein the polymeric composition comprises three mineral fillers of different types, which are an oxide, a phosphate and a silicate.

8. The composition as claimed in claim 1, wherein the weight proportion of the at least two mineral fillers relative to the total weight of the polymeric composition is greater than or equal to 1.0%.

9. The composition as claimed in claim 1, wherein the weight proportion of the at least two mineral fillers relative to the total weight of the polymeric composition is less than or equal to 50%.

10. The composition as claimed in claim 1, wherein the at least two mineral fillers are in the form of particles that have a volume-average size, measured according to laser diffraction particle size analysis, of less than or equal to 2 μm.

11. The composition as claimed in claim 1, wherein the particles of polymeric composition are present in a content ranging from 0.5% to 20% by weight, relative to the total weight of the cosmetic composition.

12. The composition as claimed in claim 1, wherein the one or more organic fluid(s) is (are) selected from the group consisting of:
    monoalcohols containing from 2 to 4 carbon atoms and polyols containing from 2 to 6 carbon atoms;
    mineral oils, vegetable oils, fatty alcohols, fatty acids, esters containing at least one fatty acid and/or at least one fatty alcohol, and silicones;
    and mixtures thereof.

13. The composition as claimed in claim 1, wherein the composition comprises at least 20% by weight of water, relative to the total weight of the composition.

14. The composition as claimed in claim 1, wherein the composition also comprises at least 5% by weight of organic fluid(s), relative to the total weight of the composition.

15. The composition as claimed in claim 1, wherein the particles of the polymeric composition have a substantially spherical shape, and have a volume-average size, measured according to laser diffraction particle size analysis, of less than or equal to 250 μm.

16. The composition as claimed in claim 1, wherein the particles of the polymeric composition have the shape of fibers having an average length less than or equal to 3 mm.

17. The composition as claimed in claim 1, wherein the composition also comprises one or more antiwrinkle active agent(s) different from the mineral fillers, selected from the group consisting of:
retinoids;
natural or synthetic peptides;
alpha-hydroxy acids and beta-hydroxy acids;
ketone acids;
hyaluronic acid, salts thereof and esters thereof.

18. The composition as claimed in claim 17, wherein the composition comprises said antiwrinkle active agent(s) in contents ranging from 0.01% to 10% by weight relative to the total weight of the composition.

19. A cosmetic treatment method for skin, the method comprising contacting the skin with a cosmetic composition as defined in claim 1.

20. A method of reducing signs of skin aging, the method comprising contacting the skin with a cosmetic composition as defined in claim 1.

21. The composition as claimed in claim 3, wherein the polyamide is selected from the group consisting of polyamide 6, polyamide 66 and copolymers of polyamide 6/polyamide 66 in any proportions.

22. The composition as claimed in claim 1, wherein the polymeric composition comprises at least three mineral fillers of different types selected from the group consisting of oxides, sulfates, carbonates, phosphates and silicates.

23. The composition as claimed in claim 4, wherein the polymeric composition comprises at least three mineral fillers of the different types.

24. The composition as claimed in claim 4, wherein the at least two mineral fillers of different types of fillers are selected from the group consisting of titanium dioxide, an alkali metal or alkaline-earth metal sulfate and a silicate.

25. The composition as claimed in claim 4, wherein the at least two mineral fillers of different types are selected from the group consisting of titanium dioxide, barium sulfate and tourmaline.

26. The composition as claimed in claim 5, wherein the three mineral fillers of different types are a titanium dioxide, barium sulfate and tourmaline.

27. The composition as claimed in claim 6, wherein the polymeric composition comprises at least three mineral fillers of different types.

28. The composition as claimed in claim 8, wherein the weight proportion in greater than or equal to 1.5%.

29. The composition as claimed in claim 8, wherein the weight proportion is greater than or equal to 2.5%.

30. The composition as claimed in claim 9, wherein the weight proportion is less than or equal to 40%.

31. The composition as claimed in claim 9, wherein the weight proportion is less than or equal to 30%.

32. The composition as claimed in claim 10, wherein the volume-average size of the particles ranges from 0.1 µm to 2 µm.

33. The composition as claimed in claim 10, wherein the volume-average size of the particles ranges from 0.2 µm to 1.5 µm.

34. The composition as claimed in claim 10, wherein the volume-average size of the particles ranges from 0.2 µm to 1 µm.

35. The composition as claimed in claim 11, wherein the particles are present in a content ranging from 1% to 15% by weight.

36. The composition as claimed in claim 11, wherein the particles are present in a content ranging from 2% to 10% by weight.

37. The composition as claimed in claim 13, wherein the composition comprises at least 30% by weight of water.

38. The composition as claimed in claim 13, wherein the composition comprises at least 50% by weight of water.

39. The composition as claimed in claim 14, wherein the composition comprises at least 10% of organic fluid(s).

40. The composition as claimed in claim 15, wherein the volume-average size of the particles ranges from 5 µm to 150 µm.

41. The composition as claimed in claim 15, wherein the volume-average size of the particles ranges from 10 µm to 50 µm.

42. The composition as claimed in claim 16, wherein the average length is less than or equal to 2 mm.

43. The composition as claimed in claim 16, wherein the average length is less than or equal to 1.5 mm.

44. The composition as claimed in claim 17, wherein the retinoids are selected from the group consisting of retinols, esters of a $C_2$ to $C_{22}$ acid and of retinol, retinal, and retinoic acids.

45. The composition as claimed in claim 17, wherein the peptides are those comprising 2 to 20 amino acids and/or amino acid derivatives.

46. The composition as claimed in claim 17, wherein the peptides are those comprising 2 to 10 amino acids and/or amino acid derivatives.

47. The composition as claimed in claim 18, wherein the content of the antiwrinkle active agent(s) ranges from 0.1% to 8% by weight.

48. The composition as claimed in claim 18, wherein the content of the antiwrinkle active agent(s) ranges from 0.5% to 5% by weight.

* * * * *